United States Patent
Atkins, Jr. et al.

(10) Patent No.: US 10,085,915 B2
(45) Date of Patent: Oct. 2, 2018

(54) SAFETY FLUID DISPENSER

(71) Applicant: ENT Solutions Group, LLC, San Antonio, TX (US)

(72) Inventors: James H. Atkins, Jr., San Antonio, TX (US); Lori Jean Atkins, San Antonio, TX (US)

(73) Assignee: ENT Solutions Group, LLC, San Antonio, TX (US)

(*) Notice: Subject to any disclaimer, the term of this patent is extended or adjusted under 35 U.S.C. 154(b) by 0 days.

(21) Appl. No.: 15/092,877

(22) Filed: Apr. 7, 2016

(65) Prior Publication Data

US 2016/0296421 A1    Oct. 13, 2016

Related U.S. Application Data

(60) Provisional application No. 62/144,017, filed on Apr. 7, 2015.

(51) Int. Cl.
| | |
|---|---|
| *A61J 1/20* | (2006.01) |
| *A61F 13/40* | (2006.01) |
| *A61J 1/18* | (2006.01) |

(52) U.S. Cl.
CPC .............. *A61J 1/2048* (2015.05); *A61J 1/18* (2013.01); *A61J 1/20* (2013.01); *A61J 1/201* (2015.05); *A61J 1/2006* (2015.05); *A61J 1/2037* (2015.05); *A61J 1/2096* (2013.01); *A61M 35/006* (2013.01)

(58) Field of Classification Search
CPC ...... A61J 1/18; A61J 1/20; A61J 1/201; A61J 1/2006; A61J 1/2037; A61J 1/2048; A61J 1/2089; A61J 1/2096; B65B 3/003; A61B 50/33; A61B 50/37; A61B 50/39; A61B 2050/375; A61M 35/006
See application file for complete search history.

(56) References Cited

U.S. PATENT DOCUMENTS

| | | | |
|---|---|---|---|
| 4,128,098 A | 12/1978 | Bloom et al. | 128/272.3 |
| 5,147,333 A | 9/1992 | Raines | 604/249 |
| 5,279,579 A | 1/1994 | D'Amico | 604/192 |
| 5,573,516 A | 11/1996 | Tyner | 604/249 |
| 5,976,115 A | 11/1999 | Parris et al. | 604/283 |
| 6,202,708 B1 | 3/2001 | Bynum | 141/9 |
| 6,482,188 B1 | 11/2002 | Rogers et al. | 604/249 |
| 6,743,214 B2 | 6/2004 | Heil et al. | 604/414 |
| 8,910,919 B2 | 12/2014 | Bonnal et al. | 251/149.1 |
| 9,101,352 B1 * | 8/2015 | Light | A61B 19/029 |

(Continued)

*Primary Examiner* — Timothy L Maust
*Assistant Examiner* — Andrew Stclair
(74) *Attorney, Agent, or Firm* — Campbell Stephenson LLP (57) ABSTRACT

An apparatus that includes a container portion and a coupler portion. The container and coupler are, in one embodiment, mated via an adapter that includes a one-way valve. The coupler includes a second one-way valve. In use, a fluid source, such as a vial, is connected to the coupler. An air source, such as a syringe is also connected to the coupler. Air from the syringe is introduced to the vial via the second one-way valve. The second one-way valve prevents fluid from the vial from being drawn into the syringe. Introduction of air from the syringe into the vial forces fluid from the vial into the container via the first one-way valve. The first one-way valve prevents the fluid from escaping the container.

17 Claims, 7 Drawing Sheets

(56) References Cited

U.S. PATENT DOCUMENTS

| | | | |
|---|---|---|---|
| 2001/0029360 A1* | 10/2001 | Miyoshi | A61J 1/2096 604/411 |
| 2001/0033890 A1 | 10/2001 | Kissling | B05D 1/00 |
| 2002/0004643 A1* | 1/2002 | Carmel | A61J 1/2089 604/86 |
| 2002/0193777 A1 | 12/2002 | Aneas | 604/411 |
| 2004/0118530 A1* | 6/2004 | Kressner | A61K 8/0208 162/109 |
| 2004/0133171 A1 | 7/2004 | Newton et al. | 604/256 |
| 2011/0062703 A1* | 3/2011 | Lopez | A61J 1/2096 285/129.1 |
| 2011/0087164 A1* | 4/2011 | Mosler | A61J 1/2089 604/87 |

\* cited by examiner

FIG. 9

SAFETY FLUID DISPENSER

RELATED APPLICATIONS

This application claims the domestic benefit under Title 35 of the United States Code § 119(e) of U.S. Provisional Patent Application Ser. No. 62/144,017, entitled "Applicator Saturation Device," filed Apr. 7, 2015, which is hereby incorporated by reference in its entirety and for all purposes as if completely and fully set forth herein.

FIELD OF THE INVENTION

This invention relates to medical instruments, in particular to preparing and using such instruments for the delivery of medications, such as those used to treat sinus, ear, laryngeal, and neck conditions.

DESCRIPTION OF THE RELATED ART

Certain medical procedures, such as some ear and sinus surgical procedures, can cause bleeding from a patient's tissue during the procedure (intraoperative). Medical professionals sometimes use one or more medical agents, such as vasoconstrictors, to help control the bleeding. One method of applying a vasoconstrictor involves first drawing the vasoconstrictor from a vial into a syringe, and then dispensing the vasoconstrictor from the syringe onto an absorbent cotton applicator, which is then applied directly to the patient's tissue. Due to the fact that the vasoconstrictor is first drawn into a syringe, this method involves the risk that the vasoconstrictor could be mistakenly injected into the patient. Injecting a vasoconstrictor into a patient can be extremely dangerous to the patient, even causing the patient's death in some cases.

BRIEF DESCRIPTION OF THE DRAWINGS

The present invention may be better understood, and its numerous objects, features, and advantages made apparent to those skilled in the art, by referencing the accompanying drawings.

While the invention is susceptible to various modifications and alternative forms, specific embodiments of the invention are provided as examples in the drawings and detailed description. It should be understood that the drawings and detailed description are not intended to limit the invention to the particular form disclosed. Instead, the intention is to cover all modifications, equivalents and alternatives falling within the spirit and scope of the invention as defined by the appended claims.

DETAILED DESCRIPTION

The present disclosure relates to a safety fluid dispenser and methods of using the safety fluid dispenser. In one embodiment, the safety fluid dispenser includes a container portion and a coupler portion. The container and coupler are, in one embodiment, mated via an adapter that includes a one-way valve. The coupler includes a second one-way valve. In use, a fluid source, such as a vial, is connected to the coupler. An air source, such as a syringe is also connected to the coupler. Air from the syringe is introduced to the vial via the second one-way valve. The second one-way valve prevents fluid from the vial from being drawn into the syringe. Introduction of air from the syringe into the vial forces fluid from the vial into the container via the first one-way valve. The first one-way valve prevents the fluid from escaping the container.

During medical procedures, such as sinus, ear, laryngeal, neck surgery, it is common to have various medical agents present in and around the surgical field. For example, various anesthetics, dyes, vasoconstrictors, and the like, can be present. It behooves medical professionals to take great care to ensure that all medicines are properly labelled to prevent accidental improper use. For example, if an anesthetic is improperly labelled, e.g., the concentration or strength is inaccurate, negative consequences can occur, such as patient discomfort and/or injury. Anytime a medicine is drawn into a syringe there exists the possibility, no matter how unlikely, that the medicine can be improperly injected into a patient. For some medicines that are not intended to be injected, e.g., medicines that could prove harmful or even fatal if injected into a patient, it would be ideal to avoid drawing the medicines into a syringe. However, in some scenarios, drawing the medicine into a syringe is conventionally deemed the most effective or only way to use the medicines.

In one scenario, a medicine, such as epinephrine, also known as adrenaline, is introduced onto one or more absorbent applicators. Epinephrine is a vasoconstrictor, so the epinephrine-soaked applicators can be used to stem blood flow by placing them in contact with a patient's tissue. One conventional manner of introducing the epinephrine onto the applicators is to draw the epinephrine from a vial into a syringe, and then expel the epinephrine from the syringe onto the applicators. The syringe is fitted with a needle to puncture the vial's seal. As can be seen, having a needle-tipped syringe loaded with epinephrine creates a risk of mistakenly injecting a patient with the epinephrine. The present disclosure relates to a device and methods of using the device that facilitates introduction of a medicine, such as epinephrine, into a container holding one or more applicators, while preventing the medicine from being introduced into a syringe.

Figure 1:
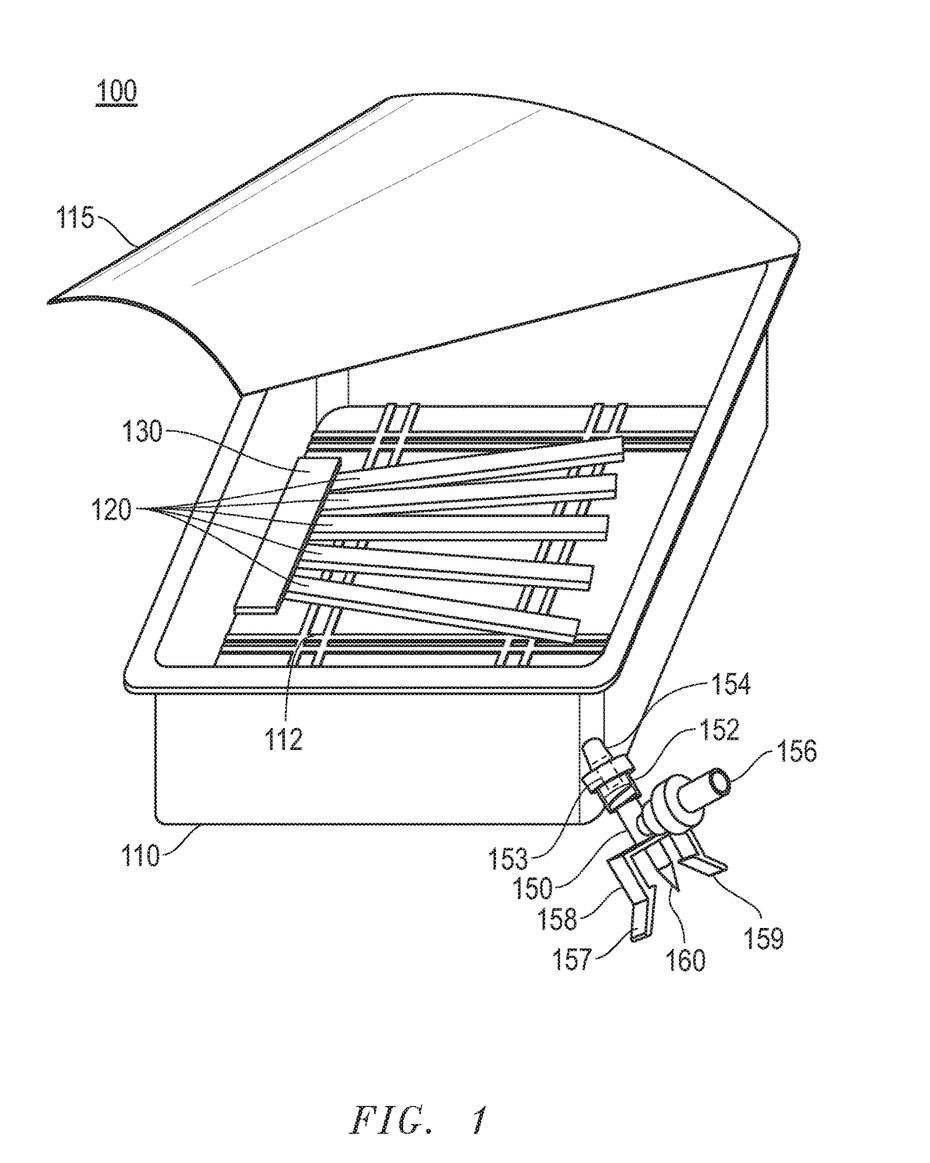
FIG. 1 illustrates a safety fluid dispenser, according to one embodiment.

FIG. 1 shows device 100. A user, such as a medical professional, of device 100 can transfer a fluid from a fluid source to a container without introducing the fluid into a syringe. As shown in FIG. 1, device 100 includes container 110, cover 115, applicators 120, positioner 130, and coupler 150. Container 110 holds applicators 120 and allows introduction of one or more medicines, such as epinephrine, that can be absorbed by applicators 120. Container 110 can be implemented as a sealed tray made of rigid plastic, semi-rigid plastic, deformable plastic, metal, cardboard, or any other synthetic or natural material suitable to hold applicators 120 and contain a fluid. The tray is, in one embodiment, substantially rectangular in shape. In one embodiment, container 110 includes one or more textured features or shape deformations 112, e.g., on one or more of the interior surfaces of container 110, to facilitate dispersion of a fluid among applicators 120. For example, features 112 can include one or more raised or recessed ribs or ridges. In another embodiment, the interior surfaces of container 110 are substantially smooth. Container 110 can be implemented using a transparent or semi-transparent material, in whole or in part. This facilitates visualization of the contents of container 110. In one embodiment, container 110 is implemented as an envelope or flexible plastic bag.

Container 110 includes an adapter 154. Adapter 154 can be implemented as a separate component configured to be affixed to container 110 or a portion of all of adapter 154 can be molded as part of container 110. In one embodiment, adapter 154 includes a fitting, such as a male Luer lock. Adapter 154 includes, in one embodiment, a normally-closed back-check valve, also referred to as a one-way valve 153, that allows fluid to enter container 110 but prevents fluid from passing through the valve to escape container 110. Back pressure on valve 153 causes valve 153 to remain closed, preventing fluid from escaping container 110 via adapter 154. This not only prevents spills, but also prevents fluids from being intentionally withdrawn from container 110, e.g., into a syringe. In one embodiment, a mechanical mechanism, such as a spring, is included in the valve to automatically close valve 153. Though described as being included in adapter 154, valve 153 can instead be included in coupler 150 (see, e.g., FIG. 3).

Adapter 154 can also include a sterile seal that can be punctured by attaching a coupler, such as coupler 150. In one embodiment, coupler 150 can be removably connected to adapter 154, e.g., by inclusion of a fitting, such as a female Luer lock, on coupler 150. In another embodiment, coupler 150 is permanently attached to container 110. For example, coupler 150 can be manufactured as an integral component of container 110. Container 110 can be fabricated in a variety of sizes and dimensions. Selection of the container size to use can be performed based evaluation of one or more criteria, such as the type of procedure and the patient's physical size. For example, a larger container with more numerous and/or larger applicators can be selected for more extensive procedures. In one example, container 110 is fabricated with the following dimensions: three inches wide by four inches long by one inch deep.

Cover 115 can be implemented using plastic, paper, or any other suitable material. In one embodiment cover 115 is implemented using clear plastic material. Cover 115 is configured to seal container 110 to preserve a sterile environment for applicators 120. Using transparent material facilitates visualization of the contents of container 110. Cover 115 can be affixed to container 110 using any suitable fastening mechanism, such as adhesive, heat seal, frictional sealing, mechanical fasteners, such as hinges, and the like.

Applicators 120 are implemented, in one embodiment, as one or more pieces of absorbent material, such as cotton or felt. Any type of natural or synthetic material may be used to form applicators 120. Applicators 120 have, in one embodiment, sponge like qualities in that applicators 120 absorb liquids. In one embodiment, applicators 120 are implemented as sterile cottonoids with or without attached strings (not shown). Strings are, in some embodiments, included with (e.g., attached to) applicators 120. A respective string can be affixed to one end of each applicator. Such strings can facilitate extraction and positioning, and are sometimes useful in preventing a user from inadvertently leaving the cottonoids in or on a surgery site. The strings can be detectable by X-Ray. In one embodiment, at least a portion of applicators 120 are color coded to indicate that they include a medicine. For example, the strings can be red to signify that a medicine is present, or blue to signify that no medicine is present. Applicators 120 can incorporate a reagent that changes color with introduction of a medicine. Various sizes of applicators 120 can be included in container 110, with multiple sizes in a single container, or a single size that varies depending on the intended use of container 110, e.g., type of procedure or patient-related criteria.

Positioner 130 holds applicators 120 in a specified position. This can improve absorption of fluid by applicators 120 and make retrieval by a user of applicators 120 from container 110 easier and/or faster, improving effectiveness and speed of the given procedure. In one embodiment, positioner 130 is attached to container 110 using, for example, a mechanical fastener, adhesive, or any other suitable coupling mechanism. In another embodiment, positioner 130 is fabricated as an integral element of container 110. Any suitable material can be used to fabricate positioner 130, such as plastic, cardboard, and the like.

Coupler 150 can be used to introduce fluid into container 110 and prevent the fluid from being drawn into a syringe. In one embodiment, coupler 150 is made of plastic, though one or more components can be rubber, metal, glass, or any other natural or synthetic material suitable for use in such medical applications. In one embodiment, coupler 150 includes a mating mechanism, such as connector 152 that enables coupler 150 to be detached from container 110. Connector 152 can be implemented as a female Luer lock fitting. Coupler 150 includes a holder 158. Holder 158 is configured to hold a fluid source, such as a vial of medicine, in place. As shown, holder 158 includes two positioning members (157 and 159) configured to mechanically grasp a vial. Holder 158 can be implemented using threaded couplers, foam, plastic graspers, adhesive, or any other suitable means of positioning and retaining a fluid source in proximity to coupler 150.

Coupler 150 includes a mechanism to gain access to fluid in a fluid source, such as piercer 160. Piercer 160 is configured to pierce a barrier of a fluid source (not shown) that prevents fluid from escaping the fluid source, e.g., a rubber stopper or cap on a vial, a suitable portion of a plastic bag, or the like. Piercer 160 can be implemented using a threaded mating mechanism. In one embodiment, piercer 160 includes a guard or safety mechanism to prevent piercer 160 from becoming contaminated and/or damaged and to protect users from inadvertent contact with piercer 160 (in contrast to, e.g., an exposed needle on a syringe). The safety mechanism can be removable, such as a plastic cap, or can be configured to automatically retract (mechanically) when piercer 160 is used to penetrate a fluid source and to automatically re-deploy when the fluid source is removed. Piercer 160 also includes one or more openings. Fluid, such as air, can be introduced to a fluid source via an opening in piercer 160, and fluid from the fluid source, such as epinephrine, can exit the fluid source via the opening.

Also included in coupler 150 is adapter 156. Adapter 156 is configured to mate to an air source, such as a syringe. In one embodiment, adapter 156 includes a threaded fitting. A slip connection can also be used. A cover or cap can be included with coupler 156 to prevent adapter 156 from becoming contaminated when not in use. The cap can be removable and reusable, or a single use cover, such as a sterile wrapping. Adapter 156 can mate to a fluid source, such as a needleless syringe containing air.

Figure 2:
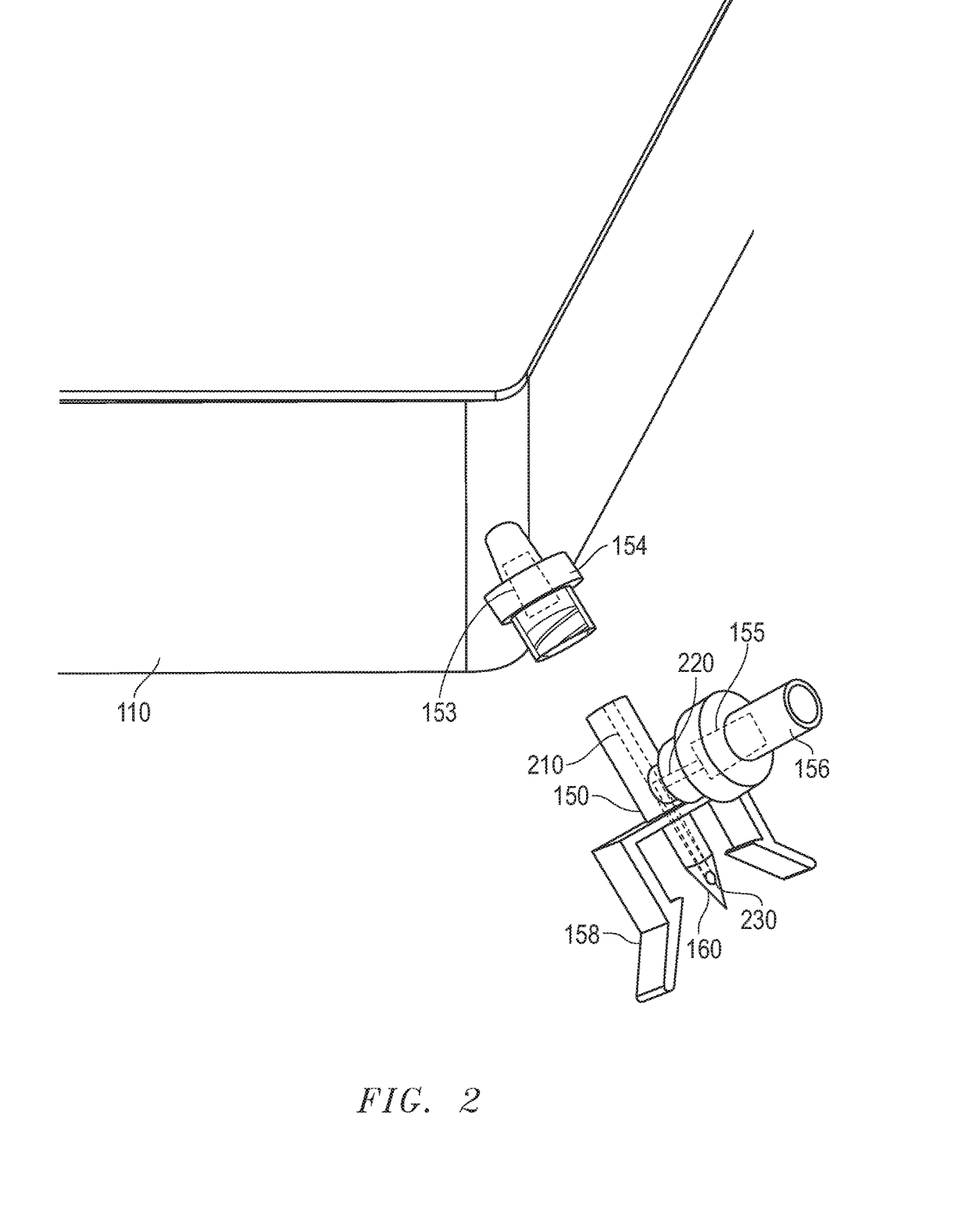
FIG. 2 illustrates aspects of a safety fluid dispenser, according to one embodiment.

FIG. 2 illustrates portions of an example safety fluid dispenser, according to one embodiment. As shown in FIG. 2, coupler 150 includes two hollow channels 210 and 220. Channel 220 has a first opening configured to admit a fluid, e.g., air, that is introduced via adapter 156. The air enters channel 220 via a one-way valve 155 and exits coupler 150 at a second end of channel 220. As shown, the second end of 220 opens near opening 230 in piercer 160. In use, channel 220 admits air from a syringe coupled to coupler 150 via adapter 156 into a fluid source, such as a vial. The vial is attached to coupler and held in place by holder 158. Piercer 160 penetrates into the fluid source. Introducing air via channel 220 forces fluid to enter channel 210, which has a first opening near opening 230. The fluid traverses coupler 150 via channel 210, and enters container 110 via a one-way valve 153 after exiting channel 210 at a second opening, which is located in proximity to adapter 154. Though the fluid that is introduced to the fluid source via adapter 156 is described as air, other fluids could be used. For example, a sterile saline solution could be introduced from the syringe into the fluid source if a user desired to dilute the medicine concurrently with dispensing the fluid.

Figure 3:
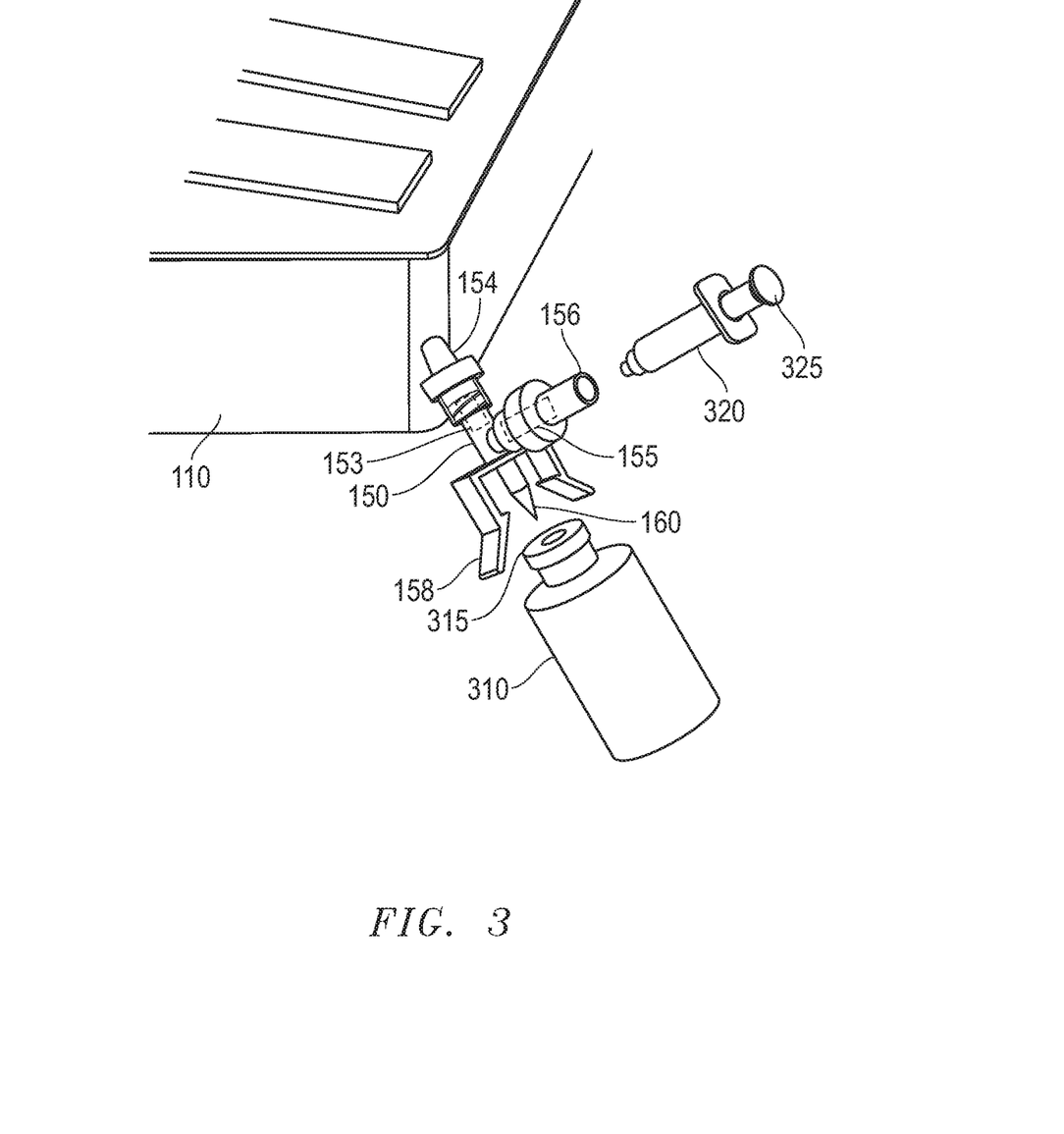
FIG. 3 illustrates aspects of a safety fluid dispenser, according to one embodiment.

FIG. 3 illustrates aspects of using device 100 of FIG. 1. As shown in FIG. 3, a fluid source 310 is mated to coupler 150. In one embodiment, fluid source 310 comprises any container suitable for holding medicinal substances, such as epinephrine. For example, fluid source 310 can be implemented as a vial with a self-sealing rubber top 315. Fluid source 310 is brought into contact with coupler 150. Piercer 160 pierces the top 315 of fluid source 310 and is brought into proximity with the fluid stored therein. Fluid source 310 is held in place by holder 158.

An air source, such as needleless syringe 320 is mated to coupler 150 at adapter 156. In one embodiment, syringe 320 is screwed onto adapter 156 using, e.g., Luer lock connectors. Syringe 320 is used to introduce air (or some other fluid) into fluid source 310 via coupler 150. For example, syringe can be filled with a desired amount of air prior to being connected to coupler 150 by pulling back plunger 325. A user then connects syringe 320 to coupler 150 and depresses plunger 325. This causes air to flow from syringe 320 into fluid source 310 via connector 156. Increasing the amount of fluid in fluid source 310 causes an increase in pressure in fluid source 310. This pressure naturally balances itself by the dispensation of a proportional amount of medicine from fluid source 310. The medicine passes through coupler 150 and into container 110 via adapter.

While syringe 320 is attached to coupler 150, plunger 325 cannot be pulled back. If a user attempts to pull back on the plunger, the coupler prevents fluid from entering the syringe. That is, (normally-closed) one-way valve 155 is included in coupler 150 allows air to flow from syringe 320 into fluid source 310 as plunger 325 is depressed. However, valve 155 prevents fluid from being drawn from fluid source 310 into syringe 320. Back pressure on valve 155, as created by pulling back on plunger 325, causes valve 155 to close, preventing fluid from being drawn from fluid source 310 into syringe 320. In one embodiment, a mechanical mechanism, such as a spring, is included in valve 155 to automatically close valve 155. In one embodiment, valve 155 is included in adapter 156, though valve 155 can be located at a point anywhere within coupler 150 that is between syringe 320 and fluid source 310 such that valve 155 prevents fluid from fluid source 310 from being introduced to syringe 320.

Figure 4:
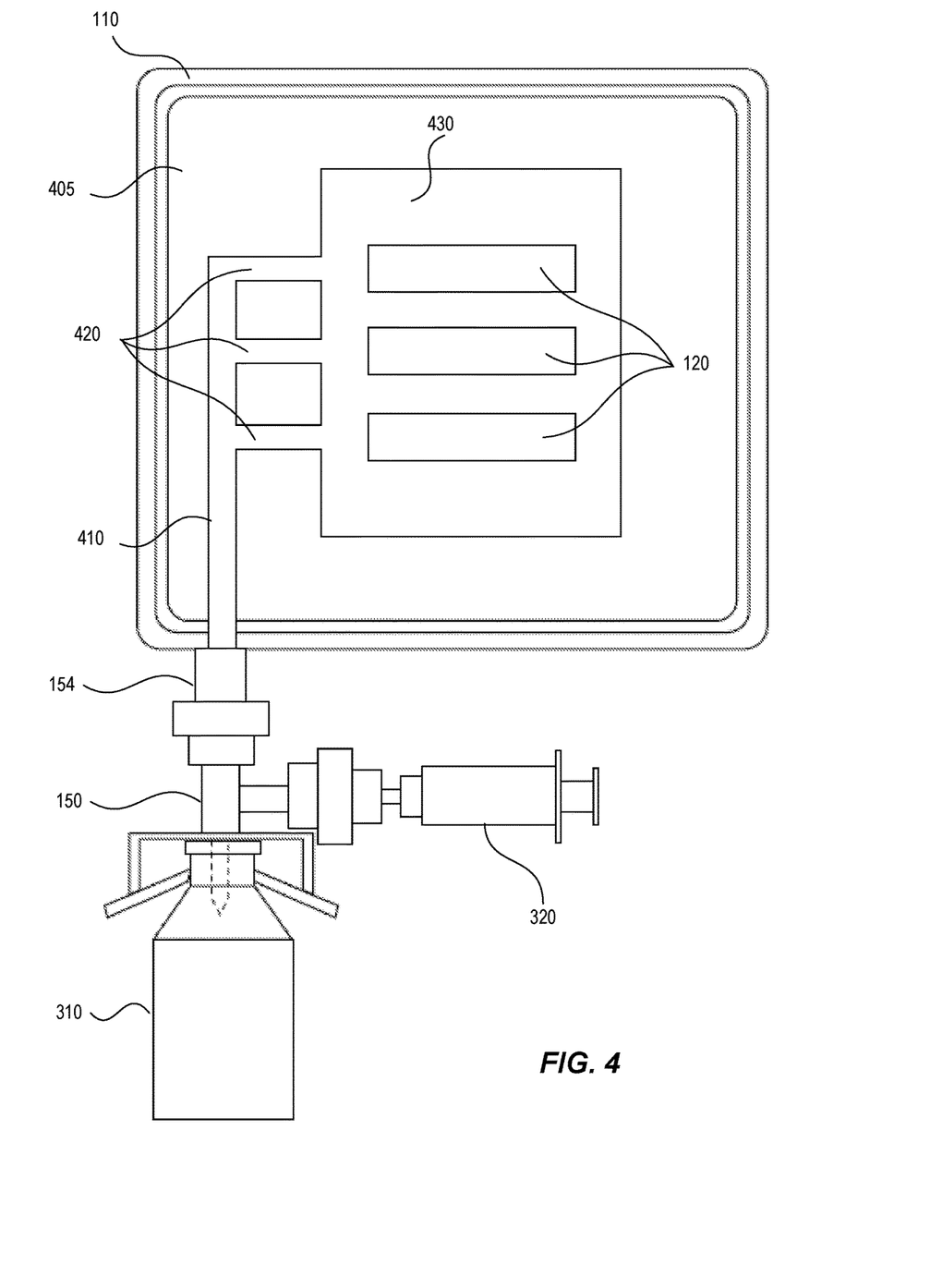
FIG. 4 illustrates aspects of a safety fluid dispenser, according to one embodiment.

FIG. 4 illustrates aspects of an example safety fluid dispenser, according to one embodiment. As shown in FIG. 4, container 110 includes recessed channels 410 and 420 and recess 430. In operation, fluid, for example epinephrine, from fluid source 310 is introduced to channel 410. The fluid can be introduced to tube 510 as a result of introducing air from syringe 320 into fluid source 310, which causes the fluid to exit fluid source 310 via coupler 150 and enter channel 410 via adapter 154. The fluid travels along channel 410 and enters recess 430 via one or more of channels 420. Channels 410 and 420, and recess 430 are recessed relative to bottom interior surface 405 of container 110. While recess 430 is shown as a single recess, in one embodiment, multiple recesses are used. For example, container 110 can include several separate recesses, e.g., a separate recess for each of several applicators 120, with a separate channel feeding into each of the several separate recesses.

Applicators 120 are positioned such that at least a portion of applicators 120 rest in recess 430. In one embodiment, applicators 120 can be held in place using a positioner (not shown). In one embodiment, applicators 120 are secured by a cover (not shown). In certain embodiments, the cover prevents applicators 120 and fluid from escaping recess 430. In one embodiment the cover is implemented as a plastic film sealed around the edges of container 110.

Figure 5:
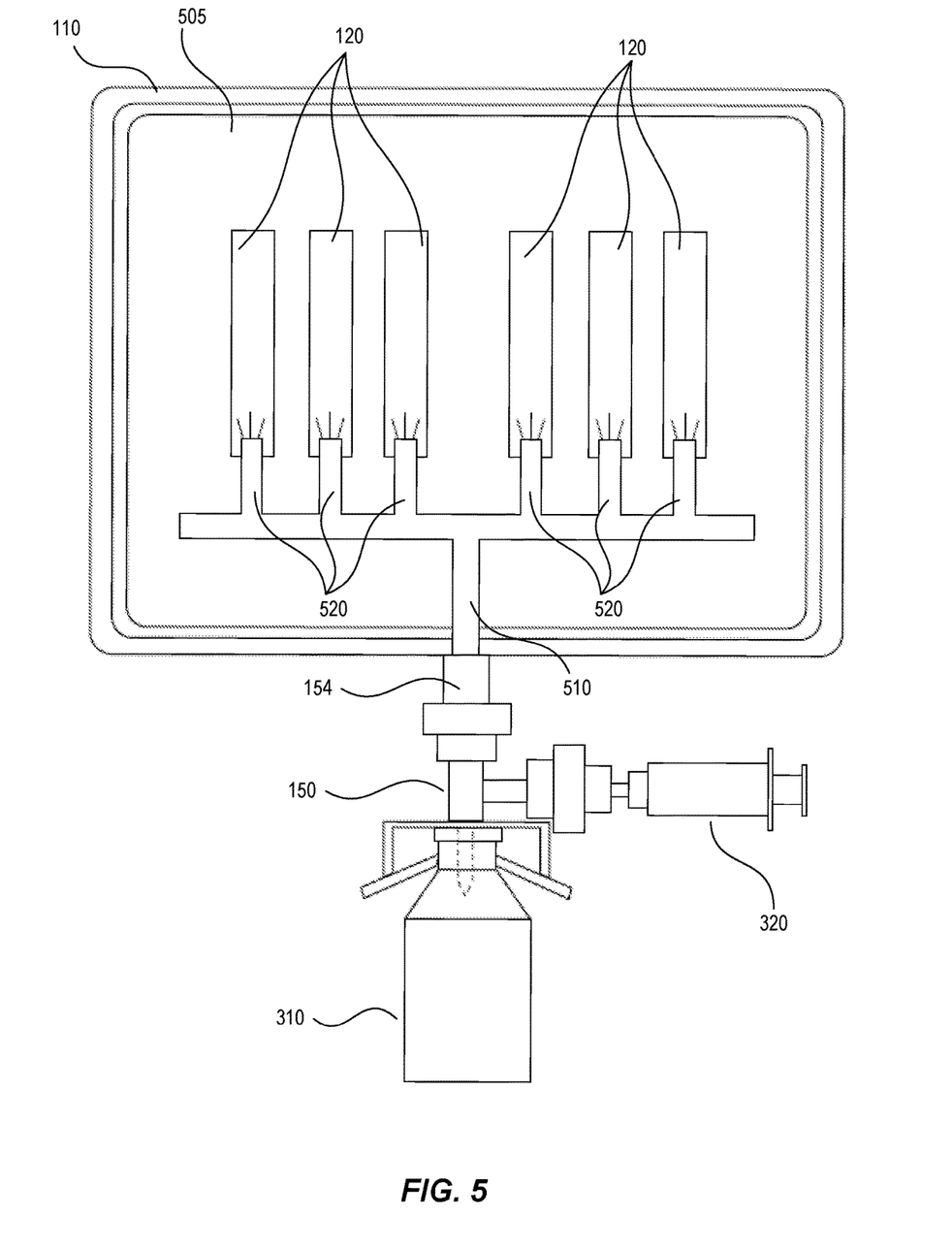
FIG. 5 illustrates aspects of a safety fluid dispenser, according to one embodiment.

FIG. 5 illustrates portions of an example safety fluid dispenser, according to one embodiment. As shown in FIG. 5, container 110 includes tubes 510 and 520. Tubes 510 and 520 are elevated relative to bottom interior surface 505 of container 110. In operation, fluid, for example epinephrine, from fluid source 310 is introduced to tube 510. The fluid can be introduced to tube 510 as a result of introducing air from syringe 320 into fluid source 310, which causes the fluid to exit fluid source 310 via coupler 150 and enter tube 510 via adapter 154.

The fluid travels along tube 510 and enters tubes 520, which branch off of tube 510. The fluid being delivered exits tubes 520 and is introduced to applicators 120. The fluid can drip, seep, or spray from tubes 520 onto applicators 120, depending on the gauge of tubes 520, the amount of fluid, and the force with which the fluid is introduced. Tubes 510 and 520 are implemented, in one embodiment, using clear plastic tubing. Any sort of conduit through which fluid can travel can be used. In one embodiment, applicators 120 can be held in place using a positioner (not shown). Also, tubes 520 can extend the length of applicators 120 (or portions thereof) with strings affixed to applicators 120 located at a distal end of applicators 120 relative to adapter 154.

Figures 6, 7, 8:
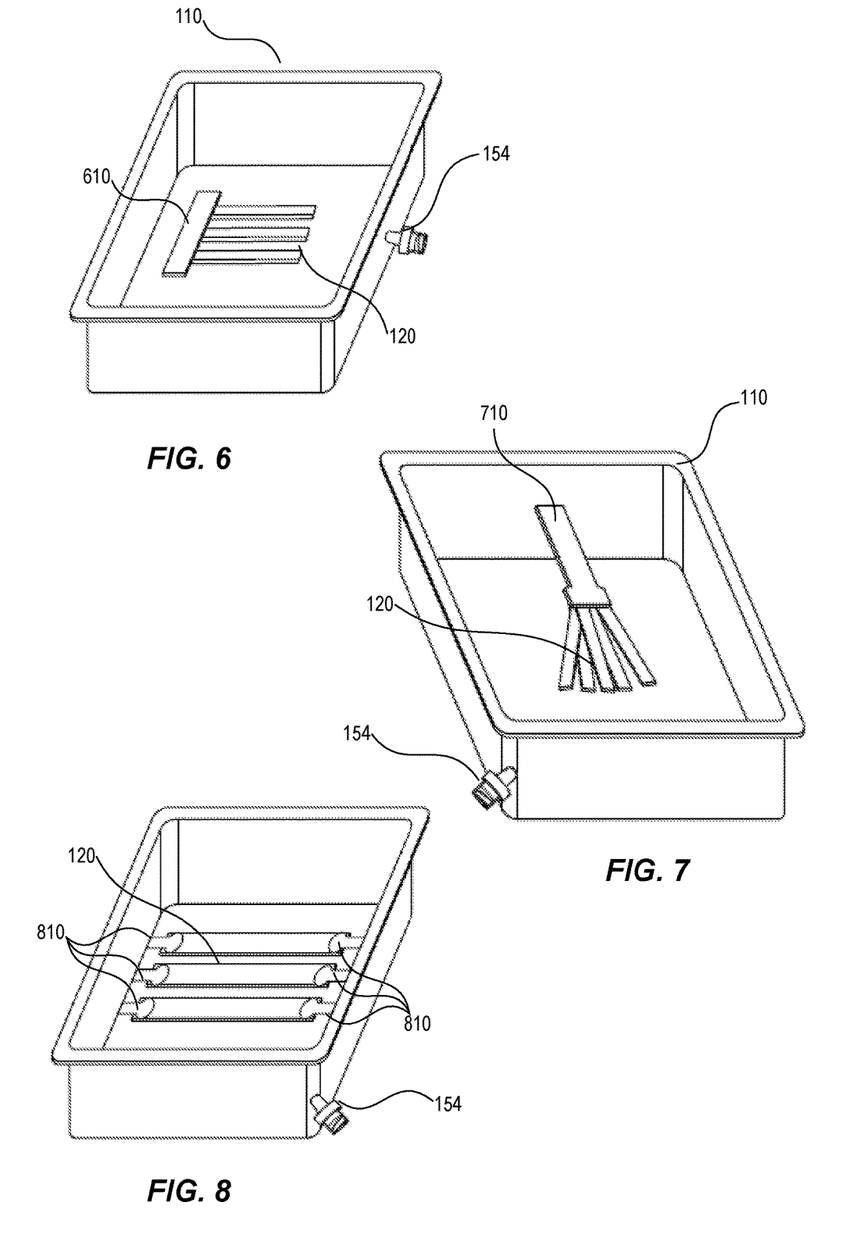
FIG. 6 illustrates aspects of a safety fluid dispenser, according to one embodiment.
FIG. 7 illustrates aspects of a safety fluid dispenser, according to one embodiment.
FIG. 8 illustrates aspects of a safety fluid dispenser, according to one embodiment.

FIG. 6 illustrates aspects of an example safety fluid dispenser, according to one embodiment. As shown in FIG. 6, container 110 includes positioner 610. Positioner 610, similar to positioner 130 of FIG. 1, holds applicators 120 in a specified position. This can improve absorption of fluid, such as epinephrine, by applicators 120 and make it easier to retrieve applicators 120 from container 110. In one embodiment, the bottom interior surface of container 110 is canted such that when container 110 is set on a flat surface, one side of the bottom interior surface is higher (farther from the flat surface) than the other side. For example, the side of the bottom interior surface in which adapter 154 makes entry into container 154 can be raised relative to the opposite side to promote absorption of fluid by applicators 120 by improving the ability of the fluid to flow throughout container 110.

In one embodiment, positioner 610 is attached to container 110. Positioner 610 can be attached to any portions of container 110, such as an interior side surface of container 110, an interior bottom surface of container, 110, or cover 115. Positioner 610 can be attached using adhesive, mechanical coupling mechanisms, or can be implemented as an integral component of container 110 (e.g., being fabricated as part of an injection molding process). Any suitable material can be used to fabricate positioner 130, such as plastic, cardboard, and the like. As shown in FIG. 6, positioner 610 maintains spacing between each of several applicators 120.

FIG. 6 also shows adapter 154. In one embodiment, a user specifies a location on container 110 for adapter 154. For example, adapter 154 can be positioned on any side of container 110, including the bottom or cover, at varying distance from a corner of container 110. The location of adapter 154 can be specified based on the type of positioning element included, the type of applicators included, or the like.

FIG. 7 illustrates aspects of an example safety fluid dispenser, according to one embodiment. As shown in FIG. 7, container 110 includes another type of positioner, positioner 710. Positioner 710 includes a single positioning element that is attached to an interior side surface of container 110.

FIG. 8 illustrates aspects of an example safety fluid dispenser, according to one embodiment. As shown in FIG. 8, container 110 includes another type of positioner, positioner 810. Positioner 810 includes several positioning elements that are attached to an interior bottom surface of container 110. As shown, positioner 810 includes two clips per applicator 120.

Figure 9:
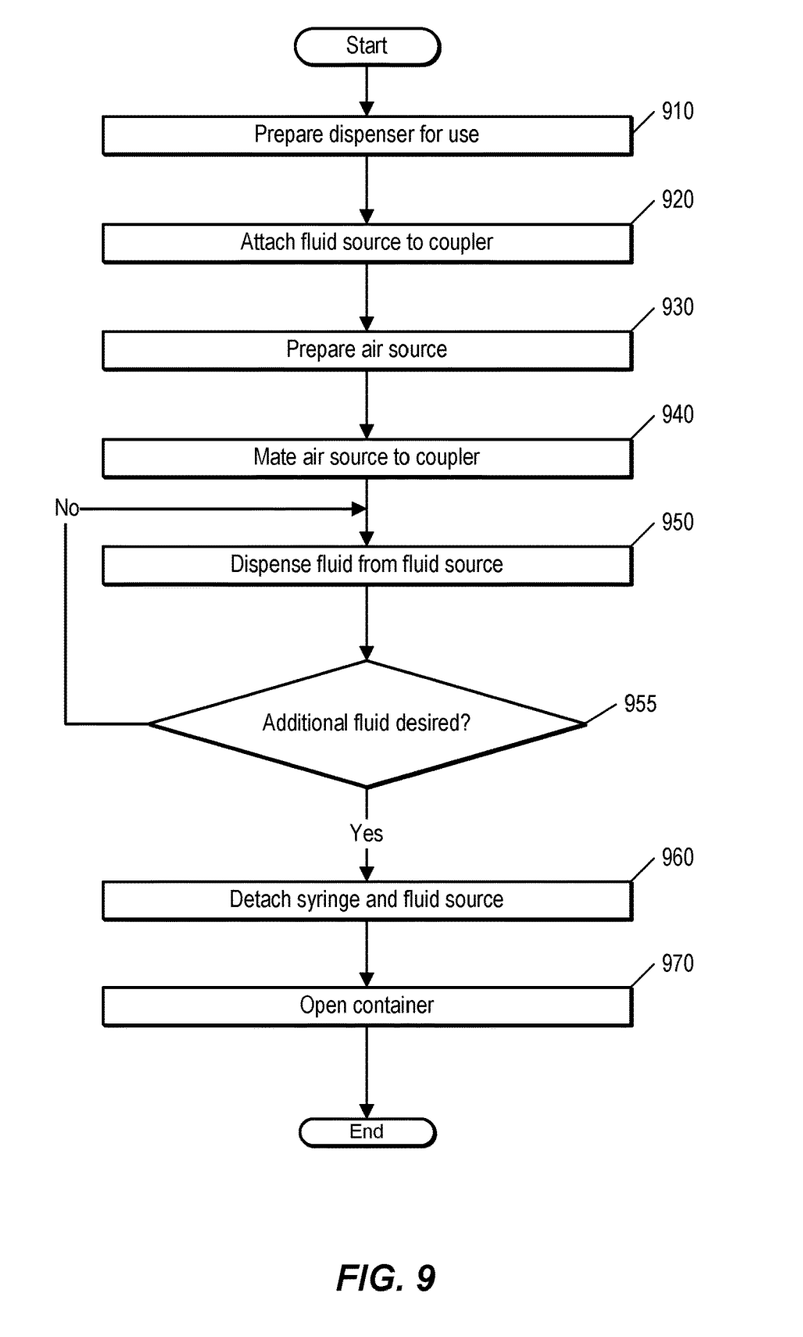
FIG. 9 is a flow diagram illustrating a method of using a safety fluid dispenser according to one embodiment.

FIG. 9 is a flow diagram illustrating a method of using a safety fluid dispenser, such as device 100 of FIG. 1, according to one embodiment. At 910, a user, such as a medical professional, prepares the device for use. In one embodiment, this involves the user attaching a coupler, such as coupler 150 of FIG. 1, to an adapter, such as adapter 156, of a container, such as container 110 of FIG. 1. In one embodiment, the coupler is already attached and the coupler and container are permanently connected. In one embodiment, the user removes the container and coupler from sterile packaging and/or breaks a seal on the container, e.g., on an adapter that is a portion of the container.

The user, at 920, attaches a fluid source to the coupler. In one embodiment, the fluid source is implemented as a vial with a self-sealing rubber stopper. The fluid source contains a medicine, such as epinephrine. Attaching the fluid source to the coupler involves, in one embodiment, piercing the fluid source using a piercer, such as piercer 160 of FIG. 1. The fluid source can be connected to the coupler via mechanical grasping elements, threaded connecters, or any other fitting or mating mechanism suitable for such medical applications.

At 930, the user prepares to dispense fluid from the fluid source, e.g., by introducing air into the fluid source. In one embodiment, the user draws a desired amount of air into a syringe by pulling back on the syringe's plunger. In one embodiment, the air is filtered prior to introduction into the fluid source to reduce possibility of contamination. The user attaches the syringe to the coupler at 940. The syringe can be mated to the coupler using, for example, threaded or slip connectors.

At 950, the user dispenses fluid from the fluid source. In one embodiment, this involves depressing the plunger on the syringe mated to the coupler. Depressing the plunger causes air from the syringe to enter the fluid source via a first entry of the coupler and pushes the fluid out of the fluid source, through a second entry of the coupler, and into the container through the adapter.

At 955, the user determines whether the applicators are sufficiently saturated. In one embodiment, this involves viewing the applicators through a clear portion of the container. The degree of saturation desired can depend on the user for which the applicators are intended. If the applicators are insufficiently saturated, the user can reorient the container such that the fluid inside the container is redistributed or flows to the insufficiently saturated applicators. In one embodiment, the user dispenses additional fluid from the fluid source, e.g., by introducing more air from the syringe into the fluid source. In response to determining that the applicators are sufficiently saturated, the user removes the syringe and fluid source at 960. The fluid source can be stored in a safe location.

At 970, the user opens the container and extracts one or more applicators, such as applicators 120 of FIG. 1. In one embodiment, the applicators are held in place by positioners, such as positioner 130 of FIG. 1. The applicators can then be used to apply the fluid as determined by the user.

Although the present invention has been described in connection with several embodiments, the invention is not intended to be limited to the specific forms set forth herein. On the contrary, it is intended to cover such alternatives, modifications, and equivalents as can be reasonably included within the scope of the invention as defined by the appended claims.

What is claimed is:

1. An apparatus comprising:
   a container, wherein
      the container comprises
         a first adapter, and
         a bottom surface comprising
            one or more recesses, and
            one or more channels, and
      the one or more recesses and the one or more channels are recessed relative to the bottom surface;
   a first valve;
   a coupler, wherein
      the coupler is attached to the first adapter,
      the first valve is configured to
         admit a fluid from the coupler into the container at the first adapter, and
         prevent fluid flow from the container into the coupler at the first adapter,
      the coupler comprises a second valve,
      the coupler is configured to transfer the fluid from a fluid source to the container via the first valve,
      the second valve is configured to prevent the fluid from the fluid source from traversing the second valve, and
      the one or more channels couple the first adapter and the one or more recesses such that the one or more channels feed the fluid from the first adapter to the one or more recesses; and
   one or more applicators, wherein
      the one or more applicators are stored in the one or more recesses.

2. The apparatus of claim 1, wherein
   the one or more applicators comprise absorbent material.

3. The apparatus of claim 2, further comprising:
   a positioner configured to secure the one or more applicators in the container.

4. The apparatus of claim 2, wherein
   the container comprises a removable cover, and
   the removable cover is configured to be sealed to preserve sterility of the container and the one or more applicators.

5. The apparatus of claim 2, wherein the container is rigid.

6. The apparatus of claim 1, wherein the first valve comprises a one-way valve configured to admit fluid to the container and prevent fluid from escaping the container via the first valve.

7. The apparatus of claim 1, wherein the second valve comprises a one-way valve configured to admit air to the fluid source and prevent fluid from escaping via the second valve.

8. The apparatus of claim 1, wherein the coupler comprises a connector configured to receive a needleless syringe.

9. The apparatus of claim 1, wherein the coupler further comprises:
   a first hollow channel configured to introduce air to the fluid source via the second valve; and
   a second hollow channel configured to dispense fluid from the fluid source to the container via the first valve.

10. The apparatus of claim 2, wherein the one or more applicators comprise one or more color codes, and the one or more color codes indicate that the one or more applicators comprise an agent.

11. The apparatus of claim 10, wherein the agent is configured to react with the fluid.

12. The apparatus of claim 1, wherein the coupler is configured to receive the fluid source, such that, upon the fluid source being attached to the coupler, the fluid is transferred from the fluid source to the container via the first valve, and the coupler is configured to dispense the fluid into the container by virtue of being configured to introduce air into the fluid source via the second valve in order to force the fluid through the first valve.

13. The apparatus of claim 8, wherein the connector is configured to permit air to be introduced via the needleless syringe.

14. The apparatus of claim 13, wherein the second valve is configured to prevent fluid from the fluid source from being drawn into the needleless syringe.

15. The apparatus of claim 9, wherein the coupler further comprises:
   a piercer configured to puncture a seal on the fluid source.

16. The apparatus of claim 1, wherein the one or more recesses are comprised in a plurality of recesses, the one or more channels comprise a plurality of channels, and each of the plurality of channels feeds into a corresponding one of the plurality of channels.

17. The apparatus of claim 1, wherein the first valve comprises a one-way valve configured to admit fluid to the container and prevent fluid from escaping the container via the first valve, and the second valve comprises a one-way valve configured to admit air from an air source into the fluid source and prevent fluid flow from the fluid source into the air source via the second valve.

* * * * *